US005952264A

United States Patent [19]

Walker et al.

[11] Patent Number: 5,952,264

[45] Date of Patent: Sep. 14, 1999

[54] CONTROL OF CRABGRASS WITH A FUNGAL PATHOGEN

[76] Inventors: Harrell L. Walker, 1171 Hwy. 3072, Ruston, La. 71270; Anthony M. Tilley, 2567 Doc Steed Rd., Minden, La. 71055

[21] Appl. No.: 08/867,711

[22] Filed: Jun. 2, 1997

Related U.S. Application Data

[63] Continuation-in-part of application No. 08/234,264, Apr. 28, 1994, Pat. No. 5,635,444.

[51] Int. Cl.$^6$ .......... A01N 63/04

[52] U.S. Cl. .......... 504/117

[58] Field of Search .......... 504/117

[56] References Cited

U.S. PATENT DOCUMENTS

| | | | |
|---|---|---|---|
| 3,999,973 | 12/1976 | Templeton | 71/79 |
| 4,390,360 | 6/1983 | Walker | 71/79 |
| 4,419,120 | 12/1983 | Walker | 71/79 |
| 4,715,881 | 12/1987 | Andersen et al. | 71/79 |
| 4,718,935 | 1/1988 | Walker et al. | 71/79 |
| 4,724,147 | 2/1988 | Marois et al. | 424/93 |
| 4,767,441 | 8/1988 | Walker et al. | 71/79 |
| 4,808,207 | 2/1989 | Gotlieb et al. | 71/73 |
| 4,818,530 | 4/1989 | Marois et al. | 424/93 |
| 5,034,328 | 7/1991 | Boyette | 435/254 |
| 5,192,541 | 3/1993 | Savage et al. | 424/93 D |
| 5,332,573 | 7/1994 | Yamaguchi et al. | 504/117 |
| 5,393,728 | 2/1995 | Charudattan et al. | 504/117 |

OTHER PUBLICATIONS

Vajna, L., "*Fusarium lateritium* Nees ex Link as a Parasite and Host in Interfungal Hyphal Interactions," J. Phytopathology 118, 157–164 (1987).

Junko Ohra, Kenji Morita, Yasuko Tsujino, Takane Fujimori, Matt Goering, Steve Evans, and Paul Zorner, "Production of Two Phytotoxic Metabolites by the Fungus *Alternaria cassiae*," Biosci, Biotech. Biochem, 59 (9), 1782–1783 (1995).

J. T. Daniel, G. E. Templeton, R. J. Smith, Jr. and W. T. Fox, "Biological Control of Northern Jointvetch in Rice With An Endemic Fungal Disease," Weed Science, vol. 21, Issue 4 (Jul.), pp. 303–307 (1973).

Guy Brown, E. H. Cole, Jr. and R. R. Nelson, "Pathogenicity of Curvularia Sp. to Turfgrass," Plant Disease Reporter, vol. 56, No. 1, p. 59 (1972).

Walker, H. Lynn, "*Fusarium lateritium*: A Pathogen of Spurred Anoda (*Anoda cristata*) Prickly Sida (*Sida spinosa*), and Velvetleaf (*Abutilon Theophrasti*)," Weed Science, vol. 29:629–631, (1981).

D. K. Crawley, H. L. Walker and J. A. Riley, "Interaction of *Alternaria macrospora* and *Fusarium lateritium* on Spurred Anoda," Plant Disease, Nov. pp. 977–979 (1985).

Strobel, Gary A. "Biological Control of Weeds." Scientific American. pp. 72–78, Jul. 1991.

*Primary Examiner*—S. Mark Clardy
*Attorney, Agent, or Firm*—Randall C. Brown; Rick Matos; Akin, Gump, Strauss, Hauer & Feld, L.L.P.

[57] ABSTRACT

A method for biological control of pest grasses such as crabgrass using the fungus *Cochliobolus intermedius* R. R. Nelson (anamorph *Curvularia intermedia* Boedijn). The fungus is applied to the grass in amounts effective to produce typical disease symptoms which kill or suppress, and thus control the grass. The fungus may be administered as a foliar application or as granules, either of which may include additives such as surfactants, glucose or starch to enhance the pathogenic action of the fungus. Four isolates of the fungus are on deposit with the Department of Biological Sciences, Louisiana Tech University in Ruston, La. and with the patent collection of the International Mycological Institute in Surrey, UK and have been assigned the numbers 361688 (MT-5), 361689 (CG-L), 375263 (MT-6) and 375264 (MT-7).

31 Claims, 1 Drawing Sheet

CONTROL OF CRABGRASS WITH A FUNGAL PATHOGEN

CROSS-REFERENCE TO RELATED APPLICATION

The present patent application is a continuation-in-part of U.S. patent application Ser. No. 08/234,264 filed Apr. 28, 1994 which is now U. S. Pat. No. 5,635,444.

FIELD OF THE INVENTION

This invention relates to bioherbicides for controlling weeds and more particularly, to a method for biological control of a variety of pest plants including crabgrass using the fungus *Curvularia intermedia* or *Cochliobolus intermedius.*

BACKGROUND OF THE INVENTION AND DESCRIPTION OF THE RELATED ART

Weeds present a tremendous problem to agricultural production throughout the world, and cause an estimated 10–12% loss of value for agricultural products in the United States, the most recent estimate being $20 billion annually (McWhorter, C. G. [1984] Weed Science, 32:850–855). Chemical pesticides are commonly used to control weeds in agricultural crops, but concern over environmental damage caused by these pesticides has recently elicited societal pressures to replace the chemical pesticides with alternative control methods. One area of active research in this area involves the use of plant pathogens, including both bacteria and fungi, to control pest plants in agricultural crops.

A major constraint to commercial development of a plant pathogen as a biological herbicide is selectivity. A pathogen that controls only one weed species in one type of crop does not have the same market potential as a pathogen that controls several important weed species in different types of crops.

Several methods are known in the art for biological control of weeds. As disclosed in U.S. Pat. No. 3,999,973, to Daniel et al., the anthracnose fungus *Colletotrichum gloeosporioides* has been used to control the weed northern jointvetch. Another strain of this fungus has been used to control winged waterpimrose. *Colletotrichum malvarum* has been used to control prickly sida. These three pathogens have been combined to control all three target weeds at once. In other experimental work the fungus *Alternaria macrospora* has been used to control spurred anoda (*Anoda cristata*), Weed Science, H. L. Walker, 1981, Vol. 29, pp. 505–507.

U.S. Pat. No. 4,390,360, dated Jun. 28, 1983, describes "Control of Sicklepod, Showy Crotalaria and Coffee Senna With A Fungal Pathogen" using the fungus *Alternaria cassiae* to produce typical weed lesions which kill or suppress the respective weeds. U.S. Pat. No. 4,419,120 dated Dec. 6, 1983, discloses "Control of Prickly Sida, Velvetleaf and Spurred Anoda with Fungal Pathogens" using the fungus *Fusarium lateritium* to kill or suppress the respective weeds. U.S. Pat. No. 4,715,881, dated Dec. 29, 1987, to Andersen, et al., details "Control of Eastern Black Nightshade with a Fungal Pathogen" using a strain of *Colletotrichum coccodes* which is pathogenic toward eastern black nightshade (*Solanum ptycanthum*). U.S. Pat. No. 4,718,935, dated Jan. 12, 1988 and U.S. Pat. No. 4,767,441, dated Aug. 30, 1988, describe a "Method For The Preparation of Mycoherbicide-Containing Pellets" characterized by alginate gel pellets containing living fungus capable of producing conidia when exposed to sufficient light and moisture. U.S. Pat. No. 4,724,147, dated Feb. 9, 1988, to James J. Marois, et al., and U.S. Pat. No. 4,818,530, dated Apr. 4, 1989, also to James J. Marois, et al., both detail the "Preparation of Pellets Containing Fungi for Control of Soilborne Diseases", in which fungi are first selected and grown for a time sufficient to produce inoculum. To prepare the pellets, the fungal propagules are harvested, homogenized, and diluted with sodium alginate solution. Pelletization is then accomplished by dropwise addition of the fungal propagule-alginate mixture into a solution of calcium chloride or calcium gluconate. The resulting alginate gel pellets containing living fungi can then be dried and used as inoculum.

U.S. Pat. No. 5,192,541, dated Mar. 9, 1993, to Steven D. Savage, et al., describes "Weed-Killing *Xanthomonas campestris*", in which novel microorganisms useful in controlling unwanted grasses and other weeds are discovered through a process which involves isolating plant pathogens from asymptomatic plants.

SUMMARY OF THE INVENTION

It has now been found that the fungus anamorph *Curvularia intermedia* Boedijn and it corresponding teleomorph *Cochliobolus intermedius* R. R. Nelson are effective in controlling multiple species of biological pathogen susceptible pest grasses in several different types of important agricultural crops. In addition to controlling crabgrass, dry weight reductions of 70% or more were noted for barnyardgrass, green foxtail, johnsongrass, wild oat, shattercane, and some other susceptible pest grasses in greenhouse tests.

Accordingly, one aspect of the present invention provides a method for the biological control of a variety of susceptible pest grasses including crabgrass, barnyardgrass, green foxtail, shattercane and other susceptible grasses comprising applying the fungus *Curvularia intermedia* Boedijn (teleomorph *Cochliobolus intermedius* R. R. Nelson) to said susceptible pest grasses in an amount effective to control said susceptible pest grasses.

The method of the invention employs a composition comprising at least one of the perfect stage fungus *Cochliobolus intermedius* and the imperfect stage fungus *Curvularia intermedia,* both of which are biological pathogens according to the invention, and an inert carrier. The composition is applied to a biological pathogen susceptible pest grass in a field in an amount effective to control, i.e. kill, damage, or suppress the growth or proliferation of, the susceptible pest grass.

In one embodiment, a composition comprising *Curvularia intermedia* conidia in a liquid surfactant such as nonoxynol (9 to 10 POE) [$\alpha$-(p-nonylphenyl)-$\omega$)-hydroxypoly (oxyethylene)], or TWEEN 80 (trademark) [oxysorbic (20 POE) polyoxyethylene sorbitan monooleate] is applied to at least one susceptible pest grass in a field in an amount effective to produce lesions which kill, damage or suppress, and thus control, the susceptible pest grass.

In a particular embodiment, the composition of the invention comprises the fungus *Curvularia intermedia,* an inert carrier and an additive which enhances the pathogenic action of the fungus. Thus, in another embodiment, a composition comprising *Curvularia intermedia* conidia and an organosilicone surfactant such as SILWET L-77 (trademark) [silicone polyether copolymer] which has been found to enhance the pathogenic action of *Curvularia intermedia,* is applied to at least one susceptible pest grass in a field in an amount effective to control said susceptible pest grass.

The composition of the invention can be formulated as a granule, foliar spray or any other conventional formulation used in the application of herbicides to crops. Granules to be used as inoculum containing the fungus can be produced, for example, by pelletization of the mycelial homogenate resulting from a submerged liquid fermentation process as described herein. It is contemplated that granular preparations of the fungus are suitable for preemergence or postemergence applications.

In addition to the pest grasses mentioned above, sicklepod together with susceptible pest grasses may also be controlled by using the fungus *Alternaria cassiae* in combination with *Curvularia intermedia.* Thus, one aspect of the invention provides a method for controlling sicklepod and at least one susceptible pest grass selected from crabgrass, barnyardgrass, green foxtail, and shattercane comprising administration of *Curvularia intermedia* in combination with *Alternaria cassiae* to said sicklepod and said at least one susceptible pest grass in a field in an amount effective to control said sicklepod and said at least one susceptible pest grass.

A composition comprising the combination of the two pathogenic fungi provides control of a broader range of pest plants than is achieved using either fungus alone. Thus, the present invention also provides an herbicidal composition for the control of sicklepod and a susceptible pest grass comprising the fungi *Alternaria cassiae* and at least one of *Curvularia intermedia* and *Cochliobolus intermedius* and an inert carrier.

Another aspect of the present invention provides a method of producing *Curvularia intermedia.* The *Curvularia intermedia* of the invention was isolated from diseased plants according to the methods described herein. Conidia of *Curvularia intermedia* can be produced during incubation in Petri dish cultures or during a two-stage process involving submerged liquid fermentation and tray culture. Conidia can be harvested from the Petri dishes using a surfactant in distilled water or by vacuuming the conidia from tray cultures.

DETAILED DESCRIPTION OF THE INVENTION

Figure 1:
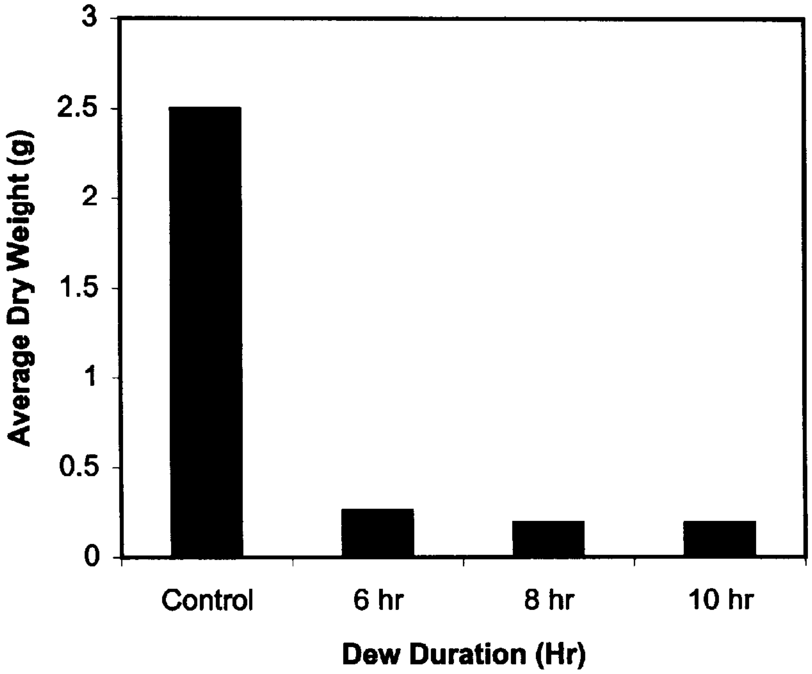
FIG. 1. Graph depicting dry weight of crabgrass plant tissue as influenced by dew duration following inoculation with *Curvularia intermedia* strain MT-5. Controls received surfactant only followed by a 10 hr. dew period. Data points are averages of four replicates.

Four isolates of the fungus *Curvularia intermedia* are on deposit with the Department of Biological Sciences, Louisiana Tech University in Ruston, La. and with the Patent Collection of the International Mycological Institute in Surrey, UK, and have been assigned the numbers 361688 (MT-5), 361689 (CG-L), 375263 (MT-6) and 375264 (MT-7).

According to Ellis, M. B. 1966. (Dematiaceous Hyphomycetes. VII. Curvularia, Brachysporium etc. Mycological Papers 106:1–57) *Curvularia intermedia* is described as follows: "Colonies on P.D.A. effused, greyish brown, cottony. Mycelium composed of branched, septate, subhyaline or rather pale brown, smooth or verruculose, 2–5 $\mu$ thick hyphae. Stromata, none seen. Conidiophores arising singly or in groups terminally and laterally on the hyphae, simple or loosely branched, straight or flexuous, often with a series of slightly thickened nodes, pale to dark brown, smooth-walled, septate, often 1 mm. and sometimes more that 1 mm. long, 5–9 $\mu$ thick. Conidia borne in clusters at the apex of the conidiophore and roughly in verticils at the nodes, straight or slightly curved, approximately ellipsoidal or broadly fusiform but always somewhat unequal-sided, 3-septate, the middle septum usually truly median and traversing the conidium at its widest point, the basal cell often the narrowest, the cell at each end usually subhyaline or pale brown, intermediate cells brown or dark brown, smooth-walled 27–40(32) $\mu$ long, 13–20(15.5) $\mu$ thick in the broadest part."

The fungal isolates used in this invention were isolated from diseased plants of crabgrass Digitaria sp.) collected from various locations. All of the strains (MT-5, CG-L, MT-6 and MT-7) of *Curvularia intermedia* were isolated on potato dextrose agar (PDA), then subcultured on vegetable juice agar. The fungus sporulated profusely on vegetable juice agar in plastic Petri dishes incubated inverted at 24° C. with 12 hour photoperiods over two, 20-watt cool-white fluorescent lights directed upwardly from 20 cm below the cultures. The fungal isolates were identified by the International Mycological Institute, Surrey, UK as *Cochliobolus intermedius* R. R. Nelson (anamorph *Curvularia intermedia* Boedijn) and assigned the numbers indicated above. It should be noted that the *Chochliobolus intermedius* fungus is the perfect stage fungus that reproduces sexually and corresponds to the *Curvularia intermedia* fungus which is the imperfect stage fungus that reproduces asexually. Both stages of the fungus are contemplated by the present invention. Thus, as used herein and unless otherwise noted, the name *Curvularia intermedia* is generally intended to refer to either one or both the perfect and imperfect stages of the fungus of the invention.

The subject cultures have been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Although the various strains of the invention were isolated from diseased plants of crabgrass (Digitaria sp.), it is contemplated that these strains can also be isolated from other diseased plants using the methods described herein or those commonly known to the skilled artisan. Such other diseased plants include, by way of example and without limitation, Cupressus sp., Juniperus sp., Plantanus sp., Zea sp., barnyard grass, green foxtail, shattercane and others.

Although each of the strains tested were isolated from crabgrass, it is contemplated that the fungus of the invention isolated from other plant sources will also exhibit pathogenicity to susceptible pest grasses. It is anticipated that all of the strains of the fungus of the invention will demonstrate different degrees of pathogenicity to different pest grasses. It is contemplated that the plant source from which a particular fungal strain is isolated need not necessarily be the plant source toward which the same strain demonstrates the greatest pathogenicity. A particular fungal strain may demonstrate a greater pathogenicity toward a susceptible pest grass other than the plant source from which it was isolated.

The MT-5, CG-L, MT-6 and MT-7 strains were isolated from crabgrass (Digitaria sp.) from the locations indicated in Table 1. However, the same strains may also be produced by genetic engineering. By first knowing the genetic code of the isolated fungal strain, a genetically engineered fungus can be developed having the same or substantially the same genetic code using genetic engineering methods well known to those of ordinary skill in the art.

As used herein, the term "pest grasses" refers to undesired or objectionable grasses or plants which can grow alongside and among lawn grasses and crop plants. Crop plants contemplated by the invention include, for example, cotton, soybean peanut, rice, barley, sorghum, wheat, rye, wild oat, corn and the like. The term "susceptible pest grasses" refers to pest grasses which are susceptible to the pathogenic activity of the fungi of the invention. The term "pathogenic fungus" refers to all of the strains of either one or both the *Curvularia intermedia* or *Chochliobolus intermedius* fungi of the invention. Given the demonstrated activity of the four exemplified strains of the fungus of the invention, one of ordinary skill in the art will recognize that all of the strains of the fungus can be used according to the invention for controlling susceptible pest grasses. Thus, the present invention contemplates all of the strains of *Curvularia intermedia* and *Chochliobolus intermedius*. Given the biology of the present fungus, it is contemplated that a composition comprising at least one of the conidia, mycelia, spores, hyphae or whole cells of the invention will be useful in controlling susceptible pest grasses.

The novel bioherbicide, or fungus, of the invention can be utilized effectively in diverse formulations, including the agronomically acceptable adjuvants and carriers normally employed for facilitating the dispersion of active ingredients for agriculture applications recognizing a known fact that the dosage, formulations, mode of application of a chemical agent, and other variables may affect its activity in any given application. Thus, the described bioherbicide can be formulated as a suspension or dispersion, in aqueous or non-aqueous media, as a dust, as a wettable powder, as an emulsifiable concentrate, as a granule, or as any of several other known types of formulations, depending on the desired mode of application. These herbicide compositions can be applied as sprays, dusts, or granules directly to the plant or its situs where herbicidal activity is desired.

Mycelia of *Curvularia intermedia* were produced in submerged liquid culture by inoculation of corn meal-soyflour-sucrose medium with conidia from cultures grown on vegetable juice agar in Petri dishes. Mycelia from submerged liquid culture were homogenized, poured into pans, and induced to sporulate by exposure to 12-hour photoperiods under 20-watt cool-white fluorescent lights suspended 40 cm above the pans. Conidia were harvested from the surface of the air-dried mycelia, dried over $CaSO_4$ for 48 hours, and stored at 4° C. Inoculum for foliar application was prepared by suspending the resulting dried spore preparations in 0.02–0.05% surfactant.

Pellets of *Curvularia intermedia* were prepared by adding sodium alginate to a mycelial homogenate from submerged liquid culture and dripping the resulting mixture into 0.25 M $CaCl_2$. The pathogen could be easily recovered from the resulting pellets after air-drying the pellets. When the pellets were subsequently moistened and exposed to light as previously described, the *Curvularia intermedia* sporulated profusely on the surfaces of the pellets. Thus, the pellets were found suitable for storage of the pathogenic fungus or for use as a granular formulation for pre-emergence or post-emergence application. Other methods for the preparation of alginate pellets including pathogenic microbes are disclosed in United States patent U.S. Pat. No. 4,718,935 to Walker et al, U.S. Pat. No. 4,724,147 to Marois et al, U.S. Pat. No. 4,767,441 to Walker et al and U.S. Pat. No. 4,818,530 to Marois et al the disclosures of which are hereby incorporated by reference in their entirety.

Granular application of *Curvularia intermedia* is not limited to the use of alginate gel pellets, but may alternatively include granules which consist of the fungus and an inert carrier such as vermiculite, corn cob grits or clay. Although the preparation of alginate pellets of *Curvularia intermedia* is described herein, it is contemplated that other formulations typically used for herbicides can be used with the fungus herein. Such other formulations are described in a variety of texts such as *Microbial Control of Weeds* (ed. David O. TeBeest; Chapman and Hall, New York; 1991) the relevant disclosures of which are hereby incorporated by reference. Such formulations can include dusts, powders, flowable formulations, suspensions, emulsions, liquids, wettable powders and the like.

In order to provide compositions in the form of dusts, granules, water dispersible powders, aqueous dispersions, or emulsions and dispersions in organic liquids, the carrier or diluent agent in such formulations may be a finely divided solid, an organic liquid, water, a wetting agent, a dispersing agent, humidifying agent, or emulsifying agent, or any suitable combination of these. Generally, when liquids and wettable powders are prepared, a conditioning agent comprising one or more surface-active agents or surfactants is present in amounts sufficient to render a given composition containing the active material, the microorganism, dispersible in water or oil.

The surface active agent which can be used according to the present invention can be a wetting, dispersing, or emulsifying agent which will assist in the dispersion of the effective composition. The surface-active agent or surfactant can include such anionic, cationic, and nonionic agents as have heretofore been generally employed in plant control compositions of similar type. Suitable surface-active agents are set forth, for example, in "Detergents and Emulsifiers" 1971 Annual by John W. McCutcheon, Inc.

Additional surface-active agents can be added to formulations to increase the ratio of surfactants:active ingredients up to as high as 5:1 by weight. Such compositions may have a greater biological effectiveness than can be expected when the components are used separately.

The carriers for solid formulations containing the fungus of the invention can be either inert or active, i.e. they can either affect or not affect the pathogenicity of the fungus of the invention. These carriers for solid formulations can also possess a desired physical property or biological or herbicidal activity. Suitable carriers for the solid formulations of the invention can include, for example, clay, talc, bentonite, calcium carbonate, diatomaceous earth, white carbon, vegetable flours, soybean flour, zeolites, kaolin clay, starch, amylopectin, cellulose, synthetic polymers, polyvinyl alcohol, polyalkylene glycol, and the like. Other substances which may be added to the formulations of the invention include, for example, sodium lignin sulfate, polyoxyethylenenonylphenyl ether, sodium dodecylbenzenesulfonate, TRITON X-100, hydrophilic (psyllium) mucilloid gel, and others.

When referring to the solid formulation of the invention, it should be understood that physical forms such as crystals, dusts, beads, powders, particulates, pellets, tablets, agglomerates, granules and the like are contemplated. The artisan of ordinary skill will be able to readily optimize a particular solid formulation for a given application using methods well known to those in the art.

Since the composition of the invention can be applied as a foliar spray, it is contemplated that a wide variety of liquid carriers such as, for example, water, organic solvents, decane, dodecane, oils, vegetable oil, mineral oil, alcohol, glycol, polyether glycol, combinations thereof and the like can be used.

The present compositions can also include other substances such as adjuvants, surfactants, binders, stabilizers and the like, which are commonly used in agricultural and horticultural pesticides, either singly or in combination as needed. As stabilizers, an antioxidant and/or a pH regulator may be used by way of example. A light stabilizer may also be used in some instances. The total content of such adjuvants may range from 0 wt. % to 80 wt. %. The content of the carrier is therefore the value which is obtained by subtracting the contents of the effective ingredients and adjuvants from 100 wt. %.

*Curvularia intermedia* as prepared herein exhibited a relatively broad host range. Crabgrass was consistently killed, damaged or suppressed by the pathogenic fungus and proved to be the species most susceptible. Other species that were also susceptible included green foxtail (*Setaria viridis*), barnyard grass (*Echinochloa crus-galli*), shattercane (*Sorghum bicolor*) and seedling johnson grass (*Sorghum halepense*). Species that were resistant or immune to the fungus of the invention included peanuts, soybean, cotton, zoysia grass, bermuda grass, centipede grass and St. Augustine grass. Responses of these crop species ranged from no symptom development to flecking of inoculated leaves, as has been reported for foliar applications of other biological herbicides. Because *Curvularia intermedia* is effective in controlling a variety of pest grasses and does not harm many important crops and grasses, the fungus has potential for use as a bioherbicide.

Since Bermuda grass, St. Augustine grass, centipede grass and zoysia grass are resistant or tolerant, *Curvularia intermedia* may also be used to control susceptible pest grasses in residential and commercial lawns, vegetable gardens, turf, field crops and the like.

FIG. 1 depicts the effect of dew duration upon the kill of crabgrass by the MT-5 fungal strain using the conditions of Example 3. It is striking that a dew time of as little as six hours is sufficient to control the crabgrass. It is contemplated that a dew time of 4–12 hours, particularly 5–10 hours, more particularly 6–10 hours, is sufficient to control a susceptible pest grass.

Figure 2:
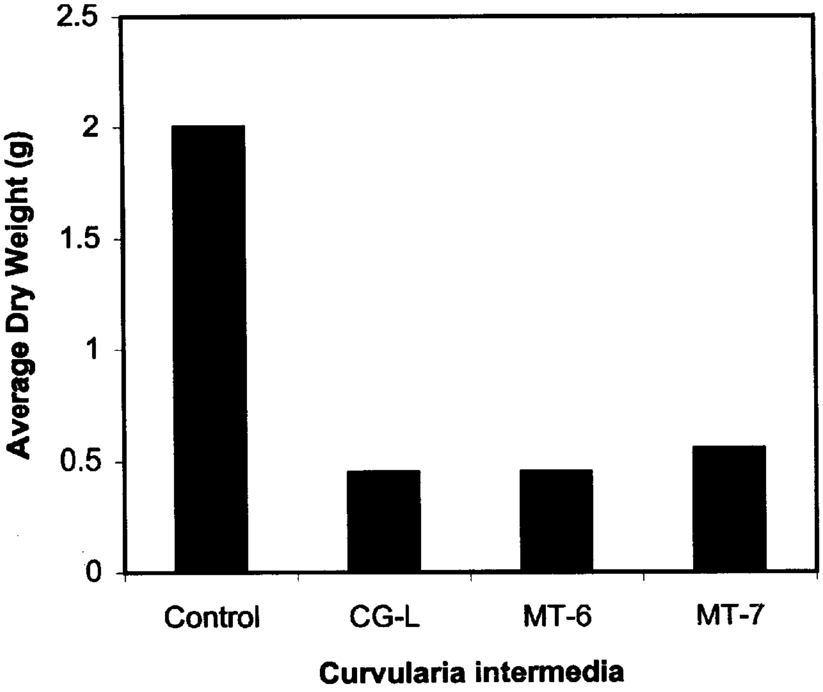
FIG. 2. Comparison of three strains of *Curvularia intermedia* for control of crabgrass. An inoculum comprising conidia (500,000 per ml) of each strain plus 0.1% (w/v) surfactant (SILWET L-77™) was applied as a foliar spray until the leaves were wet. The plants were placed in a dew chamber 25° C.) for 8 hours and then moved to greenhouse benches. Plants were harvested for dry weights 14 days after inoculation. Control plants were inoculated with surfactant only. Data points represent the average of three replicates.

FIG. 2 depicts the relative performance of the CG-L, MT-6 and MT-7 fungal strains in controlling crabgrass under the conditions described in Example 8. It is important to note that under the test conditions used, each of the three strains had substantially the same pathogenic activity against crabgrass as indicated by the recovered dry plant weight following exposure of the crabgrass to the fungus and incubation for 14 days. Given the level of pathogenicity demonstrated by each of the four different strains tested, one of ordinary skill in the art will anticipate that all strains of the *Curvularia intermedia* and *Chochliobolus intermedius* fungi will demonstrate this same behavior.

It was surprisingly found that combinations of *Curvularia intermedia* and *Alternaria cassiae* controlled crabgrass and sicklepod (*Cassiae obtusifolia*) in mixed stands that included soybeans, crabgrass and sicklepod. Example 7 details the procedure used and the results obtained. Using either separate or combined inoculation of the plants with both the respective fungi, control of both the sicklepod and crabgrass was achieved. The plants can be inoculated separately with the respective fungi or they can be inoculated simultaneously with a composition comprising a combination of the fungi.

It is understood that various additives such as, for example, glucose, surfactants or starch may be added to the inoculum preparations of *Curvularia intermedia* to enhance their pathogenic action. By the phrase "additive that enhances the pathogenic action of the fungus" is meant any compound, solvent, reagent, substance, or agent that increases the pathogenicity of the fungus as compared to the pathogenicity of the fungus in the absence of said additive. These additives may increase the susceptibility of a particular pest grass to the fungus of the invention. Additional additives contemplated by the invention include, by way of example and without limitation, herbicides, oils, hydrophobic or hydrophlic agents, ionic or non-ionic agents, agents which increase the permeability of the leaf of a pest grass to pathogens, agents which weaken the biological defenses of a susceptible pest grass to pathogens, wetting agents and the like The weed control compositions according to the present invention can contain one or more strains of *Curvularia intermedia* in combination with one or more chemical herbicides. These weed control compositions can be used in the form of mixtures with pesticides such as fungicides having no antifungal activities against *Curvularia intermedia*, insecticides and plant growth regulators, fertilizers, soil improvers and the like. Examples of usable chemical herbicides include: 2,4-dichloro-o-methylphenoxyacetic acid (2,4-D), 4-chlorophenoxyacetic acid (MCPA), 2,4,5-trichlorophenoxyacetic acid (2,4,5-T), 2-(2,4-dichlorophenoxy)propionic acid (dichlorprop), 2-(2-methyl-4-chlorophenoxy)propionic acid (mecoprop), 2-(2,4,5-trichlorophenoxy)propionic acid (fenoprop), 4-(2,4-dichlorophenoxy)butyric acid (2,4-DB), 4-(2-methyl-4-chlorophenoxy)butyric acid (MCPB), 2-(2-naphthoxy)propionanilide (naproanilide), 2-(1-naphthoxy)N,N-diethylpropionamide (napropamid), methyl (+/−)-2-[4-(2,4-dichlorophenoxy)phenoxy]propionate (diclofop-methyl), butyl 2-[4-(5-trifluoromethyl-2-pyridyloxy)phenoxy]propionate (fluazifop), methyl 2-[4-(3-chloro-5-trifluoromethylfluoromethyl-2-pyridyloxy)phenoxy]propionate (haloxyfop), 2-propynyl 2-[4-(3,5-dichloro-2-pyridyloxy)phenoxy]propionate (chlorazifop-propynyl), ethyl 2-[4-(6-chloro-2-quinoxalinyloxy)phenoxy] propionate (quizalofop-ethyl), ethyl 2-[4-(6-chloro-2-benzoxazolyl)phenoxy]propionate (fenoxaprop-ethyl), ethyl 2-[4-(6-chloro-2-benzothiazolyloxy)phenoxy]propionate (fenthiaprop-ethyl), 2,3,6-trichlorobenzoic acid (2,3,6-TBA), 3,6-dichloro-2-methoxybenzoic acid (dicamba), 2,5-dichloro-3-aminobenzoic acid (amiben), 3,5,6-trichloro-2-methoxybenzoic acid (tricamba), 4-chloro-2,2-dimethylvaleranilide (monalide), 3,4-dichloropropionanilide (propanil), 3,4-dichloro-2-methylacrylanilide (dicryl), 3,4-dichlorocyclopropanecarboxyanilide (cypromid), 3,4-dichloro-2-methylpentananilide (karsil), 3-chloro-2,4-dimethylpentananilide (solan), N-(1,1-dimethylpropynyl)-3,5-dichlorobenzamide (propyzamide), N,N-dimethyl-2,2-diphenylacetamide (diphenamide), N-naphthylphthalamic acid (naptalam), N-(1,1-dimethylbenzyl)-2-bromo-3,3-dimethylbutanamide (buromobutide), 2-benzothiazol-2-yl-oxy-N-methylacetanilide (mefenacet), N-[3-(1-ethyl-1-methylpropyl)5-isoxazolyl]-2,6-dimethoxybenzamide (isoxaben), 1,1-dimethyl-3-phenylurea (fenuron), 3-(4-chlorophenyl)-1,1-dimethylurea (monuron), 3-(4-chlorophenyl)-2,1,1-trimethylisourea (trimeturon), 3-(4-chlorophenyl)-1-methoxy-1-methylurea (monolinuron), 3-(4-chlorophenyl)-1-methyl-1-(1-methylpropyn-2-yl)urea (buturon), 3-(4-bromophenyl)-1-methoxy-1-methylurea (metobromuron), 1-(2-methylcyclohexyl)-3-phenylurea (siduron), 1,1-dimethyl-3-(3-trifluoromethylphenyl)urea (fluometuron), 3-(3,4-dichlorophenyl)-1,1-dimethylurea (diuron), 3-(3,4-dichlorophenyl)-1-methoxy-1-methylurea (linuron), 3-(3,4-dichlorophenyl)-1-n-butyl-1-methylurea (neburon), 3-(3-chloro-4-methoxyphenyl)-1,1-dimethylurea (metoxuron), 3-(4-bromo-3-chlorophenyl)-1-methoxy-1-methylurea (chlorbromuron), 3-(4-difluoro-chloromethylthio-3-chlorophenyl)-1,1-dimethylurea (fluothiuron), 3-(3-chloro-4-methylphenyl)-1,1-dimethylurea chlortoluron), 3-[4-(4-chlorophenoxy) phenyl]-1,1-dimethylurea (chloroxuron), 3-[4-(4-methoxyphenoxy)phenyl]-1,1-dimethylurea (difenoxuron), 3-[3-(N-tertiary-butylcarbamoyloxy)phenyl]-1,1-dimethylurea (karbutilate), 3-benzoyl-3-(3 , 4-dichlorophenyl)-1,1-dimethylurea (phenobenzuron), 1-alpha, alpha-dimethylbenzyl)-3-(4-methylphenyl)urea (dymron), 3-(4-isopropylphenyl)-1,1-dimethylurea (isoproturon), 3-(2-benzothiazolyl)-1,3-dimethylurea (methabenzthiazuron), 3-(2-benzothiazolyl)-1-methylurea (benzthiazuron), 3-(hexahydro-4,7-methanoindan-5-yl )-1, 1-dimethylurea (noruron), 3-cyclooctyl-1,1-dimethylurea (cycluron), 1,3-dimethyl-3-(5-trifluoromethyl-1,3,4-thiadiazol-2-yl)urea (thiazfluron), 1-(5-ethylsulfonyl-1,3,4-thiadiazol-2-yl)-1,3-dimethylurea (sulfodiazol), 3-[5-(1,1-dimethylethyl)-1,3,4-thiadiazol-2-yl]-1,3-dimethylurea (tebuthiuron), 3-(5-tertiary-butylisoxazol-3-yl)-1,1-dimethylurea (isouron), 4-[2-chloro-4-(3,3-dimethylureido) phenyl]-2-tertiary-butyl-1,3,4-oxadiazolin-5-one (dimefuron), 3-(5-tertiarybutyl-1,3,4-thiadiazol-2-yl)-4-hydroxy-1-methyl-2-imidazolidinone (buthidazole), 2-chloro-4,6-bis-(ethylamino)-1,3,5-triazine (simazine), 2-chloro-4-ethylamino-6-isopropylamino-1,3,5-triazine (atrazine), 2-chloro-4,6-bis(isopropylamino)-1,3,5-triazine (propazine), 2-chloro-4-diethylamino-6-ethylamino-1,3,5-triazine (trietazine), 2-chloro-4-ethylamino-6-tertiary-butylamino-1,3,5-triazine (terbuthylazine), 2-(4-chloro-6-ethylamino-1,3,5-triazin-2-yl-amino)2-methylpropionitrile (cyanazine), 2-chloro-4-cyclopropylamino-6-isopropylamino-1,3,5-triazine (prefox), 2-[4-chloro-4-(cyclopropylamino)-1,3,5-triazin-2-yl-amino]-2-methylpropionitrile (procyazin), 6-methoxy-2-secondary-butylamino-4-ethylamino-1,3,5-triazine (secbumeton), 6-methoxy-2,4-bis(isopropylamino)-1,3,5-triazine (prometone), 6-methylthio-2,4-bis(ethylamino)-1,3,5-triazine (simetryne), 6-methylthio-2,4-bis(isopropylamino)-1,3,5-triazine (prometryne), 6-methylthio-2-methyl amino-4-isopropylamino-1,3,5-triazine (ametryne), 6-methylthio-2-ethylamino-4-tertiarybutylamino-1,3,5-triazine (terbutryn), 6-methylthio-2-isopropylamino-4-(3-methoxypropylamino)-1,3,5-triazine (methoprotryne), 6-methylthio-2-( 1,2-dimethylpropylamino)-4-ethylamino-1,3,5-triazine (dimethametryne), 6-methylthio-2-isopropylamino-4-methylamino-1,3,5-triazine (desmetryne), 4-amino-6-tertiary-butyl-3-methylthio-1,2,4-triazin-5(4H)-one (metribuzin), 2-ethylthio-4,6-bis (isopropylamino)-1,3,5-triazine (dipropetryn), 2-tertiary-butylamino-4-ethylamino-6-methoxyamino-1,3,5-triazine (terbumeton), 2-azide-4-isopropylamino-6-methylthio-1,3, 5-triazine (aziprotryne), 4-amino-3-methyl-6-phenyl-1,2,4-triazin-5(4H)-one (metamitron), 6-tertiary-butyl-4-isobutylideneamino-1,2,4-triazin-5(4H)-one (isomethiozin), 3-cyclohexyl-6-dimethylamino-1-methyl-1,3,5-triazin-2,4-(1H,3H)-dione (hexazinone), ethyl-N-(4-chloro-6-ethylamino-1,3,5-triazin-2-yl)-aminoacetate (eglinazine), ethyl-N-(4-chloro-6-isopropylamino-1,3,5-triazin-2-yl)-aminoacetate (proglinazine), 2-chloro-N-isopropylacetanilide (propachlor), N-methoxymethyl-2',6'-diethyl-2-chloroacetanilide (alachlor), 2-chloro-2',6'-diethyl-N-(buthoxymethyl)acetanilide (butachlor), 2-chloro-2'-ethyl-6'-methyl ethyl)acetanilide (metolachlor), N,N-diaryl-2-chloroacetamide (allidochlor), 2-chloro-2',6'-dimethyl-N-(2-methoxyethyl)acetanilide (dimethachlor), 2,6-dinitro-N,N-dipropyl-4-trifluoromethylaniline (trifluralin), N-butyl-N-ethyl-2,6-dinitro-4-trifluoromethylaniline (benfluralin), 2,6-dinitro-N-propyl-N-cyclopropyl-4-trifluoromethylaniline (profluralin), N,N-diethyl-2,4-dinitro-6-trifluoromethyl-m-phenylenediamine (dinitramin), 4-isopropyl-2,6-dinitro-N,N-dipropylaniline (isopropaline), 2,6-dinitro-N-secondary-butyl-4-tertiary-butylaniline (buttalin), 4-methylsulfonyl-2,6-dinitro-N,N-dipropylaniline (nittalin), 3,4-dimethyl-2,6-dinitro-N-1-ethylpropylaniline (pendimethalin), 3,5-dinitro-4-dipropylaminobenzensulfonamide (oryzalin), N-ethyl-N-(2-methylallyl-2,6-dinitro-4-(trifluoromethyl)aniline (ethalflutalin), N,N-diethyl-2,4-dinitro-6-trifluoromethyl-m-phenylenediamine (diethamine), 2-chloro-N-(4-methoxy-6-methyl-1,3,5-triazin-2-yl-aminocarbonyl) benzenesulfonamide (chlorsulfuron), methyl 2-[3-(4-methoxy-6-methyl-1,3,5-triazin-2-yl)ureidosulfonyl]benzoate (metsulfuron-methyl), methyl 2-[3-(4,6-dimethoxypyrimidin-2-yl) ureidosulfonylmethyl]benzoate (bensulfuron), ethyl 2-[3-(4-chloro-6-methoxypyrimidin-2-yl)ureidosulfonyl]benzoate (chlorinuronethyl), methyl 3-[3-(4-methoxy-6-methyl-1,3,5-triazin-2-yl)ureidosulfonyl]-thiophenecarboxylic acid (thiameturon), Ethyl 5-[3-(4,6-dimethoxypyrimidin-2-yl) ureidosulfonyl]-1-methylpyrazole-4-carboxylate (pyrazosulfuron ethyl), 3-(4,6-dimethoxy-1,3,5-triazin-2-yl)-1-[2-(2-methoxyethoxy)-phenylsulfonyl]urea (esnosufuron), 3,7-2dichloro-8-quinolinecarboxylic acid (quinchlorac), 3,6-dichloro-2-pyridinecarboxylic acid (clopyralid), alpha-(2-chlorophenyl)-alpha-(4-chlorophenyl)-5-pyrimidinemethanol (fenarimol), S,S-dimethyl-2-(difluoromethyl)-4-(2-methylpropyl)-6-trifluoromethyl-3,5- pyridinedicarbothioate (dithiopyr), 4-chloro-5-(methylamino)-2-(3-trifluoromethylphenyl)-3 (2H)-pyridazinone (norflurazon), O,O-bis(I-methylethyl)-S-[2-(phenylsulfonyl)aminoethyl]phosphorodithioate (bensulide), (+)-2-[4,5-dihydro-4-methyl-4-(I-methylethyl)-5-oxo-1H-imidazole-2-yl]-5-ethyl-3-pyridinecarboxylic acid (imazaethapyr), 3-[5-(1,1-dimethylethyl)-3-isoxazolyl)-4-hydroxy-1-methyl-2-imidazolidione (busoxinone), 2-[1-(ethoxyimino)butyl]-3-hydroxy-5-(2H-tetrahydrothiopyran-3-yl)-2-cyclohexene-1-one (cycloxydim), S-(4-chlorobenzyl)N,N-diethylthiocarbamate (benthiocarb), S-etnyl N,N-hexamethylenethiocarbamate (molinate), isopropyl-N-phenylcarbamate (propham), isopropyl N-(3-chlorophenyl)carbamate (chloro propham), methyl N-(3,4-dichlorophenyl)carbamate (swep), 3-(ethoxycarbonylamino)phenyl N-phenylcarbamate (desmedipham), 3-(methoxycarbonylamino)phenyl N-(3-methylphenyl)carbamate (phenmedipham), S-2,3-dichloro-2-propenyl N,N-diisopropylthicarbamate (diallate), S-ethyl N,N-di-n-propylthiocarbamate (EPTC), S-ethyl N-cyclohexyl-N-ethyltiocarbamate (cycloate), methyl N-(4-aminobenzenesulfony)carbamate (asulam), S-alpha, alpha -dimethylbenzyl)piperidine-1-carbothioate (dimepiperate), S-benzyl N-ethyl-N-(1,2-dimethylpropyl)thiocarbamate (esprocarb), O-(3-tertbuthylphenyl) N-(6-methoxy-2-pyridyl)-N-methyl thiocarbamate (pributycarb), 2,4-dichlorophenyl-3-methoxy-4-nitrophenylether (chlomethoxynil), 2,4,6-trichlorophenyl-4-nitrophenylether (CNP), methyl-5-(2,4-dichlorophenoxy)-2-nitrobenzoate (bifenox), sodium 5-(2-chloro-4-trifluoromethylphenoxy)-2-nitrobenzoate (acifluorfensodium), 1-ethoxycarbonylethyl-5-(2-chloro-4-trifluoromethylphenoxy)-2-nitrobenzoate (lactofen), 5-(2-chloro-4-trifluoromethylphenoxy)-N-methanesulufonyl-2-nitrobenzamido (fomesafen), 2-chloro-2',6'-diethyl-N-(n-propoxyethyl)-acetanilide (pretilachlor), 2-(2,4-dichloro-3-methylphenoxy)propionanilide (clomeprop), 5-tert-butyl-3-(2,4-dichloro-5-isopropoxyphenyl)-1,3,4-oxadiazol-2(3H)-one (oxadiazon), 2-(3',4'-dichlorophenyl)-4-methyl-1,2,4-oxadiazolidine-3,5-dione (methazole), 3-isopropyl-1H-2,1,3-benzothiadiazin-4-(3H)one-2,2-dioxide (bentazone), 4-(2,4-dichlorobenzoyl)-1,3-dimethyl-1H-pyrazol-5-yl-p-toluenesulfonate (pyrazolate), 4-(2,4-dichlorobenzyl)-1,3-dimethyl-5-phenacyloxy-1H-pyrazole (pyrazoxyfen), 4-(2,4-dichloro-3-methylbenzyl)-1-,3-dimethyl-5-(4-methylphenacyloxy)-1H-pyrazole benzofenap), 2-(4-isopropyl-4-methyl-5-oxo-imidazolin-2-yl)-3-quinolinic acid (imazaquin), and 2-chloro-N-(3-methoxy-2-thienyl) methyl-2',6'-dimethylacetanilide (NSK-850).

It is contemplated that the fungus, or bioherbicide, of the invention and a chemical herbicide can cooperate to control a pest grass or a broader range of pest grasses better than either the fungus or herbicide alone. This cooperative behavior can be additive or synergistic. The artisan of ordinary skill can readily devise fungus/herbicide formulations containing the proper concentration or proportion of each in order to optimize the performance of a given formulation for a specific application. By applying both a fungus and an herbicide, the total amount required of each for controlling a pest grass may be decreased.

Some of the pathogenic properties of the fungus may be attributed to toxins or metabolites produced by the fungus. Accordingly, isolation of heretofore unidentified pathogenic substances secreted by *Curvularia intermedia* and application of the substances to the host plants mentioned in these studies may prove to be an effective method in controlling the plants.

Due to the selective nature of *Curvularia intermedia*, it should be understood that *Curvularia intermedia* can be used effectively to control crabgrass and other susceptible grasses in a number of different environments including, by way of example and without limitation, vegetable gardens, lawns and turf, field crops and the like.

The following examples illustrate application of the MT-5, CG-L, MT-6 and MT-7 strains of *Curvularia intermedia:*

EXAMPLE 1

Pathogen Isolation and Culture

Diseased plants of crabgrass (Digitaria sp.) were collected from various locations in Louisiana. *Curvularia intermedia* was isolated from pieces of the diseased plants using potato dextrose agar (PDA) supplemented with streptomycin sulfate (6.25 g/L) and chloramphenicol (3.75 g/L). The Petri dish cultures were inverted and incubated at 24° C., with 12 hour photoperiods. Light was provided by two 20-watt cool-white fluorescent lights that were directed upwardly from 20 cm below the cultures. In addition to *Curvularia intermedia,* several other fungi, including other Curvularia species, often grew from the diseased tissue. *Curvularia intermedia* was transferred to Petri dishes containing PDA or vegetable juice agar. The pathogen produced conidia on both media, but conidia were more abundant for cultures grown on vegetable juice agar. The table below indicates the source location for each of the four strains tested.

TABLE 1

| *Curvularia intermedia* strain | Date and Source Location in Louisiana |
|---|---|
| MT-5 | 7/1992; Webster Parish |
| CG-L | 5/1993; Lincoln Parish |
| MT-6 | 5/1994; Webster Parish |
| MT-7 | 8/1995; Webster Parish |

EXAMPLE 2

Host Range Tests

Host range tests of *Curvularia intermedia* were conducted in a greenhouse at Louisiana Tech University. Seedlings of test plants were grown in a commercially-prepared blend of peat, vermiculite and fertilizer. The size of the containers used varied from 5.5 cm square to 15 cm round, depending on the species of plants and the duration of the experiments. Inoculum for greenhouse tests was produced in Petri dishes of vegetable juice agar, as described in Example 1. Conidia were harvested using 0.02% (v/v) nonoxynol surfactant, in distilled water. Inoculum for some tests consisted of dried spore preparations suspended in 0.02–0.05% surfactant. Inoculum containing approximately $1\times10^5$ conidia per ml was sprayed to wetness onto test seedlings that were 7 to 10 days old. Control plants were sprayed with water and 0.02–0.05% surfactant only. All plants were placed in dew chambers for 8–10 hours, then moved to a greenhouse bench and observed 14 days for disease development. Susceptible plants exhibited necrotic spots and kill of leaves or plants. Crabgrass was consistently killed or suppressed by the pathogen and was the species most susceptible in these tests. Mortality of crabgrass seedlings consistently approached 90–100% within 48 hours after inoculation. Other species that were also susceptible included green foxtail (*Setaria viridis*), barnyard grass (*Echinochloa crus-galli*), shattercane (*Sorghum bicolor*), and seedling johnson grass (*Sorghum halepense*). Control of these species ranged from 60% to 80%. Species that were resistant or immune included soybeans, cotton, zoysia grass, bermuda grass, centipede grass and St. Augustine grass.

EXAMPLE 3

Cotton: Enhanced Activity of *Curvularia intermedia* With an Organosilicone Surfactant The procedure of Example 5 was repeated except that an organosilicone surfactant [Silwet L-77 (trademark), silicone-polyether copolymer, 0.05% (v/v) in distilled water] was substituted for nonoxynol, and cotton (Stoneville 453) was substituted for soybeans. Dew periods as short as 6 hours controlled 90–100% of crabgrass growing in cotton, without damage to the cotton. Use of the organosilicone surfactant resulted in a significant increase in activity when compared to results obtained using nonoxynol. Crabgrass tissue was harvested 18 days after inoculation and dried at 75° C. for 19 days. The effect of dew duration on dry weight of crabgrass tissue is presented in FIG. 1.

EXAMPLE 4

Soybean: Enhanced Activity of *Curvularia intermedia* With an Organosilicone Surfactant The procedure of Example 3 was repeated except that soybeans were substituted for cotton. Dew periods as short as 6 hours controlled 90–100% of crabgrass without damage to the soybeans. Dew periods exceeding 10 hours resulted in minor phytotoxic injury to the soybeans.

The following examples illustrate application of the CG-L isolate of *Curvularia intermedia:*

EXAMPLE 5

Selective Removal of Crabgrass From Soybeans Using *Curvularia intermedia*

Crabgrass and soybean (Cajun) seedlings were grown in mixed stands according to the conditions described in Example 2. Inoculum of *Curvularia intermedia* was prepared and applied to the crabgrass and soybean seedlings using the procedure of Example 2. Crabgrass was consistently controlled (90–100%) without damage to the soybeans.

EXAMPLE 6

Selective Removal of Crabgrass From Cotton Using *Curvularia intermedia*

Crabgrass and cotton seedlings were grown together in the same pots according to the conditions described in Example 2. Inoculum of *Curvularia intermedia* was prepared and applied to the crabgrass and cotton seedlings using the procedure of Example 2. Crabgrass was consistently controlled (90–100%) without damage to the cotton.

EXAMPLE 7

Selective Removal of Crabgrass and Sicklepod From Soybeans Using A Combination of *Curvularia intermedia* (CG-L) and *Alternaria cassiae*

Crabgrass, sicklepod and soybean (Cajun) seedlings were grown in mixed stands in pots according to the conditions described in Example 2. *Curvularia intermedia* (CG-L) and *Alternaria cassiae* were inoculated separately and in combination using the procedure of Example 2. *Curvularia intermedia* controlled only crabgrass. *Alternaria cassiae* controlled only sicklepod. The *Curvularia intermedia* plus *Alternaria cassiae* combination controlled 90–100% of the crabgrass and sicklepod without injury to the soybeans.

EXAMPLE 8

Comparison of CG-L, MT-6 and MT-7 *Curvularia intermedia* strains in Controlling Crabgrass The procedure of Example 2 was followed except that: (1)—the CG-L, MT-6 and MT-7 strains were substituted for the MT-5 strain; (2)—500,000 conidia per ml rather than 100,000 were used; (3)—1.0% SILWET rather than 0.5% SILWET was used; and (4)—the test duration was 14 rather than 18 days. The results are depicted in FIG. 2.

The above is a detailed description of particular embodiments of the invention. Those with skill in the art should, in light of the present disclosure, appreciate that obvious modifications of the embodiments disclosed herein can be made without departing from the spirit and scope of the invention. All of the embodiments disclosed and claimed herein can be made and executed without undue experimentation in light of the present disclosure. The full scope of the invention is set out in the claims that follow and their equivalents. Accordingly, the claims and specification should not be construed to unduly narrow the full scope of protection to which the present invention is entitled.

As used herein and unless otherwise specified or noted, the terms “a” and “an” are taken to mean “one” or “at least one”.

Having described the invention with the particularity set forth above, we claim:

1. A method for controlling a susceptible pest grass, comprising applying at least one of the fungus *Cochliobolus intermedius* and *Curvularia intermedia* to said susceptible pest grass in an amount effective to control said susceptible pest grass.

2. A method of claim 1 wherein said fungus is applied to said susceptible pest grass as a foliar spray comprising said fungus.

3. A method of claim 1 wherein said fungus is applied to said susceptible pest grass as granules that comprise said fungus and an inert carrier.

4. A method of claim 1 wherein said fungus is applied to said susceptible pest grass as a composition comprising said fungus, an additive that enhances the pathogenic action of said fungus, and an inert carrier.

5. A method of claim 1 wherein said fungus is *Curvularia intermedia.*

6. A method of claim 1 wherein said fungus is at least one of the strains IMI 375263 (MT-6) and IMI 375264 (MT-7) of *Curvularia intermedia.*

7. A method for controlling sicklepod and a susceptible pest grass which is at least one of a crabgrass, barnyard grass, green foxtail, and shattercane, the method comprising applying the fungi *Alternaria cassiae* and at least one of *Cochliobolus intermedius* and *Curvularia intermedia* to said sicklepod and said susceptible pest grass in an amount effective to control said sicklepod and said susceptible pest grass.

8. A method of claim 7 wherein said fungi are *Curvularia intermedia* and *Alternaria cassiae.*

9. A method of claim 8 wherein said *Curvularia intermedia* is at least one of the strains IMI 375263 (MT-6) and IMI 375264 (MT-7).

10. A method of claim 7 wherein said *Cochliobolus intermedius* and said *Curvularia intermedia* are applied separately.

11. A method of claim 7 wherein said *Cochliobolus intermedius* and said *Curvularia intermedia* are applied in combination simultaneously.

12. A bioherbicidal composition for controlling susceptible pest grasses comprising a susceptible pest grass controlling amount of at least one of the fungus *Curvularia intermedia* and *Cochliobolus intermedius* and an inert carrier.

13. A bioherbicidal composition of claim 12 wherein the at least one fungus is at least one of the strains IMI 361688 (MT-5), IMI 361689 (CG-L), IMI 375263 (MT-6) and IMI 375264 (MT-7) of *Curvularia intermedia.*

14. A bioherbicidal composition of claim 12 formulated as a foliar spray.

15. A bioherbicidal composition of claim 12 formulated as a granule.

16. A bioherbicidal composition of claim 12 further comprising an additive that enhances the pathogenic action of said at least one fungus.

17. A bioherbicidal composition of claim 16 formulated as a foliar spray.

18. A bioherbicidal composition of claim 16 formulated as a granule.

19. A bioherbicidal composition for controlling sicklepod and a susceptible pest grass comprising a sicklepod controlling amount of the fungus *Alternaria cassiae* and a susceptible pest grass controlling amount of at least one of the fungus *Cochliobolus intermedius* and *Curvularia intermedia*, and an inert carrier.

20. A bioherbicidal composition of claim 19 formulated as a foliar spray.

21. A bioherbicidal composition of claim 19 formulated as a granule.

22. A bioherbicidal composition of claim 19 wherein the composition comprises a sicklepod controlling amount of the fungus *Alternaria cassiae* and a susceptible pest grass controlling amount of at least one of the strains IMI 361688 (MT-5), IMI 361689 (CG-L), IMI 375263 (MT-6) and IMI 375264 (MT-7) of the fungus *Curvularia intermedia.*

23. A bioherbicidal composition of claim 19 further comprising an additive that enhances the pathogenic action of said at least one of the fungus *Cochliobolus intermedius* and *Curvularia intermedia.*

24. A bioherbicidal composition of claim 23 formulated as a foliar spray.

25. A bioherbicidal composition of claim 23 formulated as a granule.

26. A bioherbicidal composition of claim 23 wherein the composition comprises a sicklepod controlling amount of the fungus *Alternaria cassiae* and a susceptible pest grass controlling amount of at least one of the strains IMI 361688 (MT-5), IMI 361689 (CG-L), IMI 375263 (MT-6) and IMI 375264 (MT-7) of the fungus *Curvularia intermedia.*

27. A method for controlling a susceptible pest grass in a field comprising a crop selected from the group consisting of cotton, zoysia grass, bermuda grass, centipede grass, soybean, peanut and St. Augustine grass, said method comprising the step of:

applying at least one of the fungi *Cochliobolus intermedius* and *Curvularia intermedia* to said susceptible pest grass in an amount sufficient to control said susceptible pest grass.

28. A method of claim 27, wherein said susceptible pest grass is selected from the group consisting of crabgrass, barnyard grass, green foxtail, and shattercane.

29. A method for controlling sicklepod and a susceptible pest grass in a field comprising a crop, said method comprising the step of:

applying the fungus *Alternaria cassiae* and at least one of the fungi *Cochliobolus intermedius* and *Curvularia intermedia* to said sicklepod and said susceptible pest grass in an amount sufficient to control said sicklepod and said susceptible pest grass.

30. A method of claim 29, wherein said crop is selected from the group consisting of cotton, zoysia grass, bermuda grass, centipede grass, soybean, peanut and St. Augustine grass.

31. A method of claim 29, wherein said susceptible pest grass is selected from the group consisting of crabgrass, barnyard grass, green foxtail, and shattercane.

* * * * *